United States Patent [19]

Lindegren

[11] Patent Number: 5,170,787
[45] Date of Patent: Dec. 15, 1992

[54] DEVICE FOR POSITIONING AN ELECTRODE

[75] Inventor: Ulf Lindegren, Enskede, Sweden

[73] Assignee: Siemens Aktiengesellschaft, Munich, Fed. Rep. of Germany

[21] Appl. No.: 669,461

[22] Filed: Mar. 14, 1991

[30] Foreign Application Priority Data

Mar. 30, 1990 [SE] Sweden ................. 9001174
Jun. 15, 1990 [SE] Sweden ................. 9002130

[51] Int. Cl.5 .......................... A61B 5/04; A61N 1/05
[52] U.S. Cl. .................................. 128/642; 128/772; 128/786; 606/129; 604/280
[58] Field of Search ............... 128/639, 642, 784-786, 128/419 P, 772; 604/280, 281; 606/129

[56] References Cited

U.S. PATENT DOCUMENTS

| | | | |
|---|---|---|---|
| 3,802,440 | 4/1974 | Salem et al. ............... | 128/772 |
| 3,847,140 | 11/1974 | Ayella ............... | 128/772 |
| 4,136,703 | 1/1979 | Wittkampf . | |
| 4,448,561 | 12/1984 | Doring . | |
| 4,677,990 | 7/1987 | Neubauer . | |
| 4,860,757 | 8/1989 | Lynch et al. ............... | 128/772 |

Primary Examiner—Lee S. Cohen
Assistant Examiner—Brian L. Casler

[57] ABSTRACT

For simplifying the positioning of electrodes inside living bodies, a positioning device has a wire running through a tube, the tube being fastened to a case and being fastened to a handling element disposed in the case. With the handling element, the wire can be moved relative to the tube, which enables the positioning of an electrode in, for example, the heart, by extending a preshaped curve at the end of the wire and turning it to a suitable position. Alternatively, the tube may be fastened to the handling element and moved relative to the wire which may be fastened to the case, or relative to a second turnable handling element in the case. The preshaped curve of the wire is released by pulling the tube back from the wire.

10 Claims, 2 Drawing Sheets

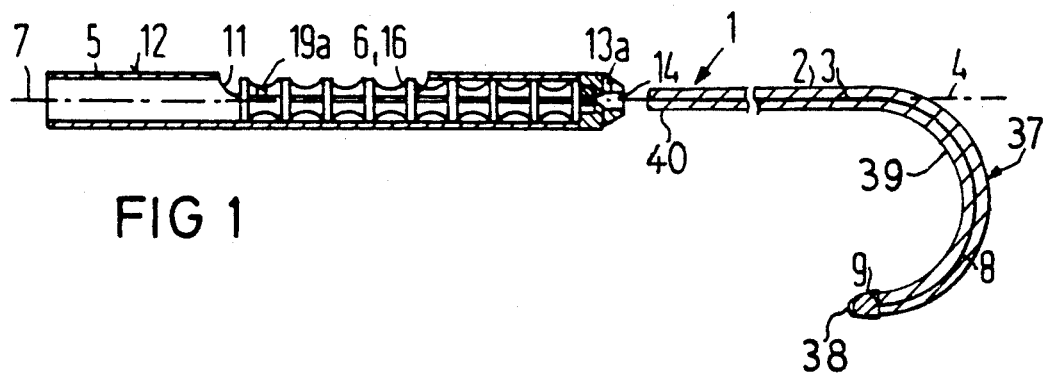
FIG 1
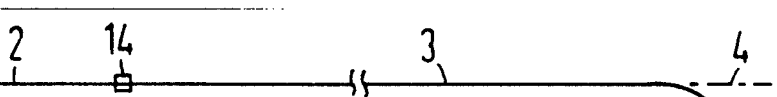
FIG 2
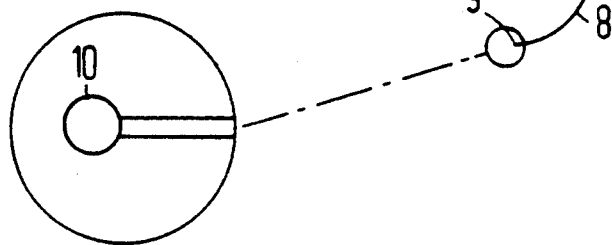
FIG 3
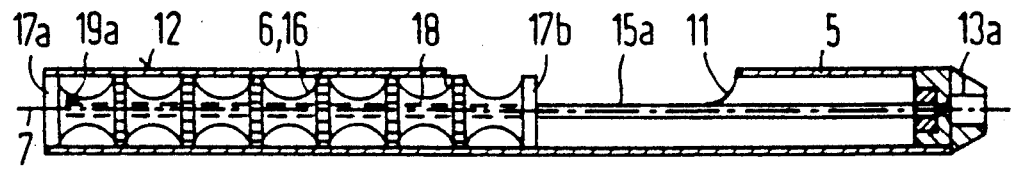
FIG 4
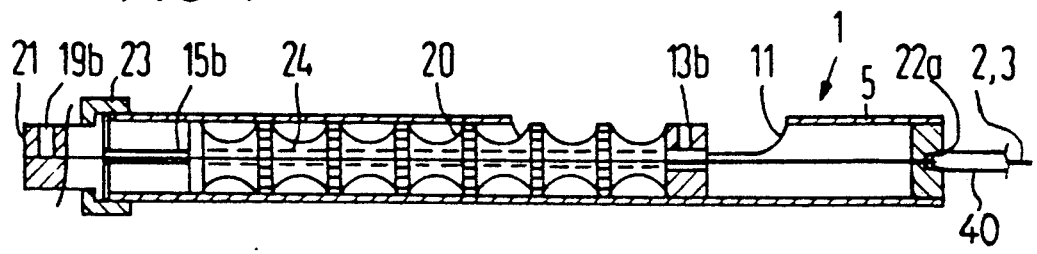

DEVICE FOR POSITIONING AN ELECTRODE

BACKGROUND OF THE INVENTION

1. Field of the Invention

The invention relates to a device for positioning an electrode inside a living body, which electrode includes an electrode head (distal end), a hollow lead and a proximal end. In particular, the invention relates to a device having a wire with a preshaped curve in one end, a flexible, but compared to the wire resistant, tube in which the wire is placed, whereby the wire and the tube are movable relative to each other, and a handle to which one end of the tube is fastened and in whose area the other end of the wire is accessible.

2. Description of the Prior Art

A device is described in U.S. Pat. No. 4,136,703, and relates to implantation of an electrode in the atrium of a heart. The device, also known as a stylet, consists of a flexible tube in which a wire with a suitable preshaped curve is placed, whereby the wire and the tube together form a double stylet wire. When the preshaped curve of the wire is inside the tube, it will be restrained from assuming its preset shape and, when it is positioned outside the tube, it will assume its preset shape. The tube is fastened to the handle through which the wire runs to be accessible for adjustment of its position in the tube. When the double stylet wire together with the electrode is moved down into the heart, the physician can, by extending a larger or smaller part of the preshaped end of the wire, position the electrode head in a suitable position.

The handling of the known device is, however, not without problems. The physician using the device needs one hand for the handle and with the other hand he shall adjust the position of the wire in relation to the tube and also have full control of the electrode. The wire could easily be deformed by the handle where it is completely unprotected. Further, it should be noted that the physician is wearing gloves which easily get wet and slippery of bodily fluids at an ongoing operation of a patient. This makes the handling of the device and the positioning of the electrode head more difficult.

SUMMARY OF THE INVENTION

The object of the invention is to provide a device that can be easily steered and controlled with one hand for the positioning of an electrode inside a living body and that minimizes the risk of deformation of the wire.

The problem is solved in accordance with the invention in that, for the above mentioned device, the handle comprises a case in which a handling element is movably arranged along the axis of the case, whereby either the wire is fastened to the handling element and the tube to the case or the tube fastened to the handling element and the wire to the case.

The physician can hold the case in one hand and with the same hand gain complete control of the lateral position of the wire and the tube relative to each other, and, by turning the case gain full control of the positioning of the electrode. Therefore, either the wire is moved relative to the tube or the tube is moved relative to the wire.

In a further embodiment of the invention, the case is provided with an opening in its mantle through which the handling element is accessible. The opening in the case makes the handling element easily movable with the thumb. The advantage of the opening in the case is more clear if compared to other possibilities, such as for instance only part of the handling element being inside the case or the case being formed as a half cylinder in which cases managing the device is more difficult as the case cannot be held as securely in the hand as it can with an opening for managing the handling element.

Further advantages with the invention are obtained when the handling element is arranged rotatably around the axis of the case. With the wire fastened to the handling element, the operator can turn the wire and move its lateral position relative to the tube at the same time.

A further advantage is obtained if the handling element has a continued part extending through the opening in the case, which part surrounds the case in an approximately ring-shaped fashion. It is hereby much easier for the operator to move the handling element laterally.

In a further embodiment of a device according to the invention, the handling element has a hole through which the wire runs, the wire is fastened to a second handling element that is attached to the case, and the second handling element is arranged rotatably around the axis of the case. The wire being fastened to the second handling element gives the possibility of turning the wire relative to the tube without turning the case.

To reduce the risk of the wire being deformed when handling the device, a guiding tube is fixed in the case, the wire runs through the guiding tube and the guiding tube and the handling element telescopically enclose each other.

For a device according to the invention, it is an advantage that the wire and the tube are removably fastened to the device so that they can be exchanged.

For a device where the wire is fastened to the handling element, the removable fastening of the wire advantageously consists of a fastening element that is accessible through the opening in the case when the handling element is moved into a particular position relative to the case.

As, for the device where the tube is fastened to handling element, the double stylet wire protruding from the case is of a defined length, it is advantageous to provide the case with a locking arrangement for the proximal end of the electrode, thereby making it easier for the operator to work with the electrode during the introduction into the heart and to position the electrode head.

To prevent the end of the wire to damage the lead when the double stylet wire is inserted into the electrode via its proximal end, the end is made with a rounded tip, for example in the shape of a ball. By making the diameter of the ball larger than the inner diameter of the tube, the ball will, for a device according to first modification, prevent the wire from being moved back beyond the end of the tube, and, for a device according to the second modification, it will prevent the tube from being moved forward beyond the ball.

DESCRIPTION OF THE DRAWINGS

FIG. 1 shows a cross-section of the device according to a first embodiment of the invention.

FIG. 2 shows a double stylet wire.

FIG. 3 shows an enlargement of the handle in FIG. 1.

FIG. 4 shows a cross-section of a handle according to a second embodiment of the invention.

DESCRIPTION OF THE PREFERRED EMBODIMENTS

Figure 5:
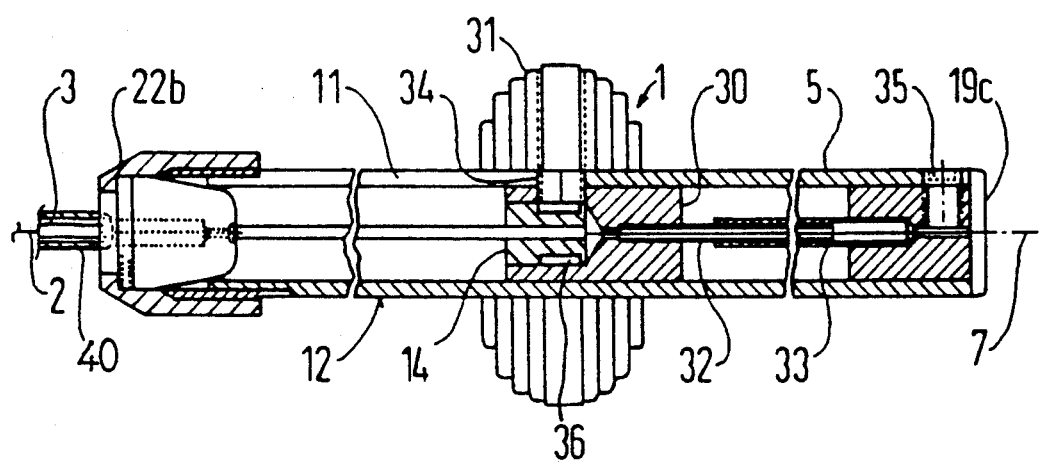
FIG. 5 shows a cross-section of a handle according to a third embodiment of the invention.

FIGS. 1-3 show a first embodiment of the device 1 according to the invention with a wire 2 that freely runs in a flexible or deformable tube 3 along its axis 4. The wire 2 and the tube 3 thereby together form a double stylet wire, which is shown in FIG. 2. The tube 3 is removably fastened to a cylindrical case 5. The wire 2 is removably fastened to a handling element 6, which is movable along and turnable around the axis 7 of the case 5. For the positioning of an electrode 37, comprising an electrode head 38 (distal end), a hollow lead 39 and a proximal end 40, the major part of the double stylet wire combination 2 and 3 is inside the electrode.

The wire 2 has a preshaped curve 8 in its free end, which in this embodiment is shaped like a J, and, by allowing a major or a minor part of the preshaped curve 8 outside the tube 3, a suitable bend of the hollow lead is obtained. By turning the wire 2 around the axis 4 of the tube 3 by means of the handling element 6, the electrode head 38 will be moved along an arc of a circle which is formed when the end 9 of the wire 2 is turned around the axis 4 of the tube 3 and thereby the electrode head 38 can be positioned more accurately at the implantation area.

As shown in FIG. 2, the wire 2 has in its end 9 a rounded tip 10 which, in this embodiment of the invention, is shaped like a ball, whose diameter is larger than the inner diameter of the tube 3 and smaller than the inner diameter of the hollow lead 39 of the electrode 37. The ball 10 will protect the lead when the double stylet wire combination 2 and 3 is inserted into the electrode 37 through its proximal end 40 and will also prevent the wire 2 from sliding backwards out of the tube 3 and thus acts as a stop for the handling element 6.

The case 5, which is preferably made of a lightweight metal or a composite material to be as light as possible, has an opening 11 in its surface 12 to make the handling element 6 accessible. The opening 11 is made for easy positioning with the thumb of the handling element 6 in a variety of ways when holding the case 5 in the hand. The removable fastening of the tube 3 is in the front end of the case 5. This embodiment of the invention shows the attachment with a screw 13a. To avoid damaging the tube 3 when mounting the tube 3, it is provided with a protection ring 14. The protection ring 14 can in its turn be provided with a thread to lock the protection ring 14 to the case 5.

In the front end of the case 5, a guiding tube 15a is arranged between the tube 3 and the handling element 6. The guiding tube 15a has a double function; protecting the wire 2 from being damaged from the outside and acting as an extra guide for the handling element 6 in the case 5 and for the wire 2 in the tube 3. The risk that the wire 2 will be deformed has thereby substantially been reduced.

In this embodiment of the invention, the handling element 6 is made as a segmented piston 16. The two end segments 17a and 17b have slightly a larger diameter than the other segments and provides the handling element 6 with gliding and guiding surfaces in the case 5. The other segments facilitate the moving of the handling element 6 in the lateral direction of the case 5, and a knurled pattern in the segments facilitate the turning of the handling element 6 in the case 5.

The handling element 6 also has a blind hole 18 which is made for the gliding of the handling element 6 on the guiding tube 15a. A fastening element 19a for the removable fastening of the wire 2 could for example be a screw and is arranged in the rear end of the handling element 6. FIG. 1 shows that the fastening element 19a is accessible from the outside through the opening 11 in the case 5.

FIG. 4 shows the device 1 according to a second embodiment of the invention. The major differences compared to the device according to FIGS. 1 and 3 is that the tube 3 is fastened to the handling element 20 and the wire 2 is fastened to a second handling element 21, which is arranged in the case 5.

The case 5 still has an opening 11 in its surface 12, but the front part of the case 5 here has a locking device 22a for the proximal end of the electrode 37. In this embodiment, the locking device 22a is in the shape of a cone in which the proximal end 40 is held.

At the other end of the case 5, the second handling element 21 is arranged to turn the wire 2 around the axis 4 of the tube 3. The second handling element 21 is connected to the case 5 via a fastening arrangement 23 allowing the second handling element 21 to be turned around the axis 7 of the case 5. The fastening arrangement 23 can be a snap, a screw or other type of arrangement so that the second handling element 21 can be fastened against the case 5. The fastening of the wire 2 to the second handling element 21 is done like in the first embodiment of the invention, according to FIG. 3, i.e., with a fastening element 19b, for example a screw.

The handling element 20 is, in the second embodiment of the invention according to FIG. 4, shaped as a segmented piston, in a way similar to the handling element 6 in FIG. 3, and moves the tube 3 relative to the wire 2. The handling element 20 does not, however, need to be turnable relative to the case 5 and can therefore be constructed more specifically for its purpose. The removable fastening 13b of the tube 3 in one end of the handling element 20 is constructed in a way similar to what has been described previously in connection with the first embodiment of the invention, for example with a screw 13b.

Also in the second embodiment, a guiding tube 15b is arranged in the case 5; in this case in the rear end of the case 5 by the other handling element 21. The handling element 20 is provided with a hole 24 compatible with the guiding tube 15b, so that the wire 2 is protected and so that the handling element 20 can glide on the guiding tube 15b.

In FIG. 5, a third embodiment of the device 1 according to the invention is shown. Also in this embodiment the tube 3 is moved relative to the wire 2, which makes this embodiment similar to the second embodiment shown in FIG. 4; the major difference being, however, that this device does not have the second handling element 21. The positioning of the electrode head 38 is done by turning the hole device 1.

To make the moving of the handling element 30 easier and more controllable, the device 1 has an outer operating handle 31, which is connected to the handling element 30 through the opening 11 of the case 5. The connection consists of a connecting element 34, which is threaded on the inside for the removable fastening of the tube 3. By providing the protection ring 14 with a channel 36, into which a screw that locks the protection ring 14 laterally to the handling element 30 can pass, the effect of the handling element 30 being pulled towards the inner surface of the case 5 is avoided.

Similar to what is shown in previous embodiments, the wire 2 is removably fastened to a fastening device 19c within the case 5. A screw 35 locks the wire 2 laterally. Because the handling element 30 is shorter in this embodiment than in previous embodiments, the telescopic arrangement to protect the wire 2 is somewhat different. In this embodiment, there are two guiding tubes 32 and 33, which are arranged so that the first guiding tube 32 is fastened to the handling element 30 and the second guiding tube 33 is fastened to the fastening device 19c within the case 5. The first guiding tube 32 runs inside the second guiding tube 33 and wire 2 is well protected within the guiding tubes 32, 33.

As in FIG. 4, this device also has a locking arrangement 22b for the proximal end of the electrode 37. In this embodiment, however, the locking arrangement 22b is constructed as a chuck that locks the proximal end 40 when the locking arrangement 22b is screwed onto the case 5.

Although modifications and changes may be suggested by those skilled in the art, it is the intention of the inventor to embody within the patent warranted hereon all changes and modifications as reasonably and properly come within the scope of his contribution to the art.

I claim as my invention:

1. A device for in vivo positioning of an electrode having an electrode head at a distal end, a hollow lead and a proximal end, said device comprising:
   a wire having a pre-shaped curve at a distal end and surrounded by a tube with said wire being movable in said tube, said tube being deformable, but mechanically resistant compared to the wire, said tube having a diameter and length adapted to be inserted into said hollow lead, said wire and said tube constituting adjustment elements and each of said wire and said tube having a proximal end; and
   a case having a handling element disposed therein so as to be movable along a longitudinal axis of said case, the proximal end of one of said adjustment elements being connected to said case and the proximal end of the other of said adjustment elements being connected to said handling element, so that the position of said distal end of said wire in relation to said tube, and thus the curvature of said distal end of said electrode in which said wire and said tube are inserted, can be selected by moving said handling element along said longitudinal axis.

2. A device as claimed in claim 1 wherein said case has an opening therein permitting manual access to said handling element for moving said handling element.

3. A device as claimed in claim 2 wherein said handling element has a projection extending through said opening in said case, said projection annularly surrounding said case.

4. A device as claimed in claim 1 wherein said handling element includes means for mounting said handling element in said case so that said handling element is rotatable around said longitudinal axis of said case.

5. A device as claimed in claim 1 further comprising an additional handling element disposed in said case, and wherein said handling element has a bore therein through which said wire runs said longitudinal axis, said wire being fastened to said further handling element and said further handling element being mounted in said case so as to be rotatable around said longitudinal axis.

6. A device as claimed in claim 1 further comprising a guiding tube disposed in said case with said wire running through said guiding tube, said handling element and said guiding tube being telescopically engaged.

7. A device as claimed in claim 1 further comprising means for removably attaching one of said adjustment elements to said case and for attaching the other of said adjustment elements to said handling element.

8. A device as claimed in claim 7 wherein said case has an opening therein permitting manual access to said handling element for moving said handling element, and wherein said means for removably fastening said wire to said handling element is accessible through said opening when said handling element is moved to a selected position within said case.

9. A device as claimed in claim 1 further comprising locking means in said case for said proximal end of said electrode.

10. A device as claimed in claim 1 wherein said pre-shaped curve terminates at said distal end of said wire with a rounded tip, said rounded tip having a diameter larger than an inner diameter of said tube.

* * * * *